United States Patent [19]

Celino, deceased et al.

[11] Patent Number: 4,639,467

[45] Date of Patent: Jan. 27, 1987

[54] ANTIBIOTIC CRISMAICIN A AND COMPOSITIONS THEREOF

[76] Inventors: Martin S. Celino, deceased, late of Lucena City; by Cecilio Celino, administrator, Antonio Larrauri, administrator, both of San Pablo City, Laguna, all of Philippines

[21] Appl. No.: 722,207

[22] Filed: Apr. 11, 1985

Related U.S. Application Data

[63] Continuation-in-part of Ser. No. 603,621, Apr. 25, 1984, abandoned.

[51] Int. Cl.$^4$ ................ C07D 493/04; A61K 31/365
[52] U.S. Cl. .................................... 514/468; 549/298
[58] Field of Search ....................... 549/298; 514/468

[56] References Cited

U.S. PATENT DOCUMENTS

| | | | |
|---|---|---|---|
| 3,524,865 | 8/1970 | Hoeksema | 549/298 |
| 3,632,607 | 1/1972 | Meyer | 549/298 |
| 4,199,514 | 4/1980 | Omura et al. | 549/298 |
| 4,237,057 | 12/1980 | Kraus | 549/298 |

*Primary Examiner*—Jane T. Fan
*Attorney, Agent, or Firm*—Flehr, Hohbach, Test, Albritton & Herbert

[57] ABSTRACT

A novel Micromonospora strain is provided which produces Crisamicin, a complex having gram positive antibacterial and antiviral activities. Crisamicin contains as major components compounds Crisamicin A and Crisamicin B, and minor amounts of compounds Crisamicin C, D and E.

8 Claims, No Drawings

ANTIBIOTIC CRISMAICIN A AND COMPOSITIONS THEREOF

This is a continuation-in-part of Ser. No. 603,621 filed Apr. 25, 1984, now abandoned.

The present invention is directed to a novel antibiotic and antibiotic complex isolated from a Micromonospora strain.

The genus Micromonospora belongs to one of the better known genera of the Actinomycetales. Members of this genus found in soils, manures, composts and lake bottom mud sediments are known to produce a variety of useful antimicrobial substances of different chemical structures. The present invention provides a novel antibiotic compound and antibiotic complex produced by a Micromonospora strain designated *Micromonospora purpureochromogenes* var. celinoensis.

It is an object of the present invention to provide a novel antibiotic and antibiotic complex having gram positive antibacterial and antiviral activities.

It is a further object of the present invention to provide a novel Micromonospora isolate RV-79-9-101, having ATCC Deposit No. 39664.

It is a further object of the present invention to provide a method for producing a novel antibiotic by fermentation of Micromonospora strain RV-79-9-101.

These and other objects of the present invention will be apparent from the following description of the specific embodiments.

The present invention provides the substantially pure compound of the following formula:

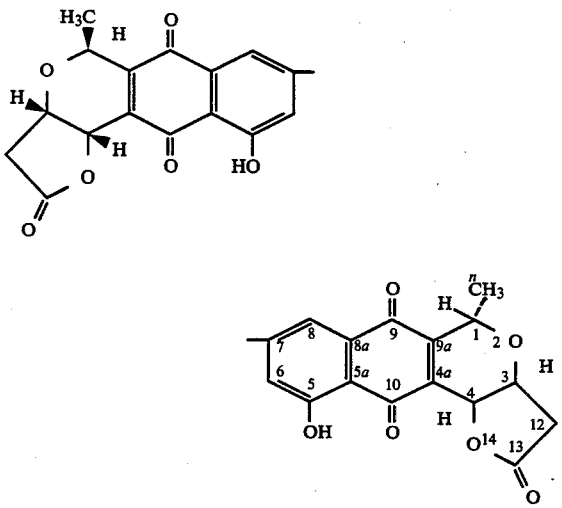

having gram positive antibacterial and antiviral activities. The present invention also provides complexes having the aforementioned compound as a major component, which are produced by Micromonospora strain RV-79-9-101, ATCC Deposit No. 39664, known as *Micromonospora purpureochromogenes* var. celinoensis.

DESCRIPTION OF THE MICROORGANISM

The strain RV-79-9-101 was isolated from a mud sample obtained from the lowland rice fields located in the San Crispin Barrio, San Pablo City, Luzon, Republic of the Philippines. Strain RV-79-9-101 has physical characteristics resembling that of *Micromonospora purpureochromogenes* but is distinguishable therefrom in its ability to produce an antibiotic having the formula indicated above.

The strain RV-79-9-101 may be selected from a conventional slant. The single colonies of dark brown-black color may be isolated and grown on medium 6B comprising 0.5% yeast extract, 0.5% N-Zamine type A, 1.0% glucose, 2.0% soluble starch, 0.1% calcium carbonate, 1.5% agar and tap water to 1 liter, pH adjusted to 7.0. Strain RV-79-9-101 grows well in shake cultures and to a more limited extent in stationary liquid or on solid cultures. On stationary agar, it produces a brown-purple diffusible pigment when observed in the light.

Strain RV-79-9-101 may be maintained in a lyophilized state or in a frozen state in vials containing sporulating suspensions of microbial culture maintained in liquid 6B medium stored under nitrogen. Plugs of agar slant cultures may also be maintained at −5° C. Strain RV-79-9-101 is maintained at the research laboratories of Mikrokar, N.V., Lucena, Luzon, Republic of the Philippines. The culture of this microorganism has also been deposited with the American Type Culture Collection, Rockfield, Md. under Deposit No. 39664.

Isolation of the Antibiotic Complex Crisamicin

The antibiotic complex according to the present invention, termed Crisamicin, may be extracted from a fermentation medium of RV-79-9-101 by extraction with organic solvents, such as chloroform or ethyl acetate. Two or three half volume extractions with a water-immiscible organic solvent will remove the majority of the antibiotic complex as determined by antimicrobial assay. The course of the antibiotic production and purification procedures may be followed using antibacterial assay employing a strain of *Staphylococcus aureus*, ATCC No. 6538P. This test bacterium may be maintained on nutrient agar slants and grown in nutrient broth for the preparation of antibiotic assay agar plates.

Organic solvent extracts of RV-79-9-101 may be concentrated under vacuum to yield an oily pigmented residue. Repeated extractions of the oily residue with small aliquots of hexane will result in an amorphous highly pigmented solid. The oily solid may be repeatedly extracted with acetonitrile to produce extracts of increasingly greater purity of Crisamicin A, the compound of the above given formula which comprises a major component of Crisamicin. The fractions of high Crisamicin A content may be combined and concentrated to a dry residue under vacuum to produce an amorphous yellow solid residue which may be crystalized from dioxane to yield yellow orange needles.

These yellow orange needles of Crisamicin A or Crisamicin complex may be applied to silica gel G60 thin layer chromatographic plates and developed with different systems. The developed plates reveal a number of biologically active zones as tested by *Staphylococcus aureus*, ATCC 6538P. With the solvent system: benzene-glacial acetic acid (9:1, V/V) Crisamicin A exhibited a zone of antimicrobial inhibitory activity at $R_f=0.20$. An additional component, termed Crisamicin exhibited biological activity at $R_f=0.12$. Minor antimicrobial components, called Crisamicin C, D and E, respectively, were evident at $R_f$ 0.08, 0.04 and 0.00. With the solvent system: chloroform-methanol-glacial acetic acid (100:5:V/V/V) Crisamicin A and B exhibited biological activity at $R_f=0.55$ and 0.48, respectively.

Crisamicin A may also be obtained in a highly pure state by high performance liquid chromatography (HPLC). In a Waters Associates Chromatographic M-6000A pump coupled to an Altex Ultrasphere-ODS (particle size 5 micrometers) column, 250 MMX 10 MMID by a Rheodyne 7125 injector the retention time of Crisamicin A was 8 minutes 10 seconds using a solvent system of acetonitrile:water (70:30, V/V). The flow rate of the mobile phase was 3.0 ml/min. with the detector wavelength set at 254 nm, sensitivity 0.1 AUFS (variable wavelength ultraviolet detector). A Linear Recorder Chart operating at chart speed of 40 cms per hour was used.

Characterization of Crisamicin A

Crisamicin A, as well as the other components of Crisamicin complex, show acid-base indicator properties, colored red in acid and blue-violet in base. The structure of Crisamicin A is given in the above formula having a molecular weight of 598.

The field desorption mass spectrum at 24 mA shows a molecular ion at m/z 598 and other ions at m/z 554, 540, 510 and 496. High resolution field desorption mass spectral measurement showed a molecular ion at 598.1124 which agrees with the empirical formula $C_{32}H_{22}O_{12}$ (Calc. 598.1111).

Ultraviolet Spectrum of Crisamicin A

Maxima (CHCl$_3$): 442 nm ($\epsilon$12,500), 268 nm ($\epsilon$34,700), 241 nm ($\epsilon$31,700);

Maxima (CH$_3$CN): 435 nm ($\epsilon$11,800), 267 nm ($\epsilon$32,800), 231 nm ($\epsilon$37,500) and 215 nm ($\epsilon$28,600).

Infrared Spectrum of Crisamicin A

KBr: 2970 cm$^{-1}$, 2930, 1795, 1670, 1650, 1625, 1550, 1510, 1400, 1370, 1285, 1260, 1240, 1200, 1160, 1140, 1100, 1080, 1065, 1035, 1000, 980, 945, 910, 890, 865, 835, 805, 790, 765, 740, 720, 700, 670.

Proton nmr Spectrum of Crisamicin A 11.88 (singlet), 7.96 (doublet, J=1.6 Hz), 7.63 (d, J=1.6 Hz), 5.26 (d, J=2.9 Hz), 5.18 (quartet, J=6.8 Hz), 4.72 (dd, J=4.5, 2.8 Hz), 3.00 (dd, J=17.8, 5.0 Hz), 2.66 (d, J=17.7 Hz), 1.55 (d, J=7.0 Hz).

Carbon nmr Spectrum of Crisamicin A (in CD$_2$Cl$_2$) 187.6 (singlet in off-resonance spectrum), 182.3(s), 174.4(s), 162.4(s), 151.4(s), 146.8(s), 135.0(s), 132.7(s), 123.2(d), 118.6(d), 115.0(s), 68.8(d), 67.3(d), 67.0(d), 37.2(triplet), 18.6(quartet).

Melting point of Crisamicin A: decomposes Optical rotatory dispersion (ORD) curve of Crisamicin A shows a negative Cotton effect with a trough [Φ]−7841 at 353 nm and a peak [Φ]+10977 at 280 nm (c 5.72× −3, CH$_3$CN).

Biological Activity

The Crisamicin complex, which consists primarily of components Crisamicin A and Crisamicin B, is active against gram positive bacteria with little or no activity against gram-negative bacteria and fungi. A spectrum of activity is shown between in TABLE 1.

TABLE 1

| Antimicrobial Spectrum of Crisamicin A | |
|---|---|
| Microorganism | Minimal Inhibitory Concentration* (micrograms per ml.) |
| Bacillus subtilis ATCC6633 | 0.5 |
| Bacillus subtilis ATCC7972 | 0.5 |
| Bacillus lichiniformis ATCC14580 | 1.0 |
| Staphylococcus aureus ATCC6538P. | 1.0 |
| Striptococcus faecalis ATCC14506 | 2.5 |
| Escherichia coli ATCC25922 | >50.0 |
| Pseudomonas aeruginosa ATCC27853 | >50.0 |
| Serratia marcescens ATCC9986 | >50.0 |
| Candida albicans ATCC18527 | >50.0 |
| Saccharomyces cerevisiae ATCC9763 | >50.0 |
| Mucor rouxii IMRU80 | >50.0 |

*Streak Dilution Assay

In addition, Crisamicin A has inhibitory activity against viruses. This activity includes antiviral activity against herpes simplex virus, VSV virus and vaccinia virus.

Production of Crisamicin

Crisamicin as a complex and Crisamicin A may be produced by the fermentation of RV-79-9-101. The microorganism may be normally maintained on agar slants of 6B medium. To produce the Crisamicin complex, agar slant cultures may be employed initially for the preparation of fermentation inoculum in liquid 6B medium. Preferably, the slant culture may be transferred to about 50 ml of sterile liquid 6B medium in a 250 ml flask to prepare an inoculation culture. The culture may be maintained for about 3 days at 28° C. on a rotary shaking culture apparatus at 150 to 250 revolutions per minute.

An alternative inoculum medium may consist of about 2% soybean flour, 1% cornstarch, 0.5% calcium carbonate and tap water to 1 liter adjusted to pH 7.0.

The standard liquid 6B medium may also be used in fermentation. For example, inoculation medium (about 10% by volume) may be used to inoculate liquid 6B medium. Maintaining the culture at 28° on a rotary shaking culture apparatus at 150 to 200 revolutions per minute will result in a fermentation broth which is antimicrobial against Staphylococcus aureus after 3 days of fermentation.

Crisamicin as a complex and purified Crisamicin A may be isolated from the fermentation broth as described above.

The fermentation may be performed in conventional large scale fermentation apparatus, such as large vessels and tanks utilizing methods and apparatus known in the art.

The compounds disclosed herein, including Crisamicin (the complex), and Crisamicins A, B, C, D and E may be formulated and administered in accordance with conventional procedures for formulating and administering pharmaceuticals. The Crisamicin compound or complex may be formulated for administration to the target site (i.e., the site of infection or potential infection or the tumor site) in the form of ointments, creams, oils, sprays and the like, or may be formulated for intravenous, or other parenteral modes of administration by using conventional liquid carriers such as sterile saline or glucose solutions. Also, the compounds according to the present invention may be formulated into pharmaceutical compositions suitable for oral administration, such as in the form of capsules or tablets. Capsules may comprise any conventional pharmaceutically acceptable materials such as gelatin, cellulose derivatives and the like. Tablets may be formulated in accordance with conventional procedures employing solid carriers, lubricants and the like which are well known in the art. Examples of solid carriers include starch, sugar, bentonite and the like.

The quantity of effective dose supplied by each dose unit form (i.e., capsule, tablet, unit injection) will usually be relatively unimportant since the total dosage may be obtained by administration by a unit dose or a plurality of unit dose forms. The pharmaceutically effective amount of compound will depend upon the extent and type of the infection. Effective doses will additionally usually vary depending upon the weight of the subject as well as the individual characteristics of each subject. It is expected that the compositions will generally be administered in a dosage range from about 1 milligram to about 100 milligrams active ingredient per kilogram of body weight per day.

It is claimed that:

1. A substantially pure compound having the formula:

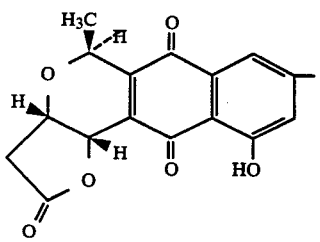

2. A biologically pure complex having antibacterial activity against gram positive bacteria
    *Bacillus subtilis* ATCC6633
    *Bacillus subtilis* ATCC7972
    *Bacillus lichinformis* ATCC14580
    *Staphylococcus aureus* ATCC6538P.
    *Streptococcus faecalis* ATCC14506
wherein said complex comprises as a major component a compound having the following formula:

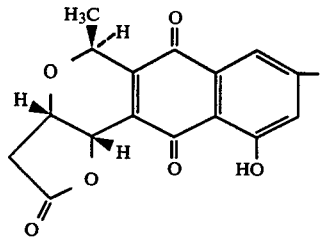

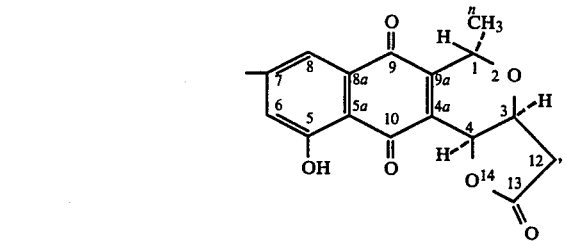

3. An antibiotic composition comprising an effective amount of a compound according to claim 1 in a pharamaceutically acceptable carrier.

4. An antibiotic composition comprising an effective amount of a complex according to claim 2 in a pharmaceutically acceptable carrier.

5. A method of prophylactic treatment of infection by gram positive bacteria in a mammal comprising the step of administering to said mammal an antibiotically effective amount of a compound according to claim 1.

6. A method of prophylactic treatment of infection by gram positive bacteria in a mammal comprising the step of administering to said mammal an antibiotically effective amount of a complex according to claim 2.

7. A method of prophylactic treatment of infection by virus in a mammal comprising the step of administering to said mammal an antivirally effective amount of a compound according to claim 1.

8. A method of prophylactic treatment of infection by virus in a mammal comprising the step of administering to said mammal an antivirually effective amount of a complex according to claim 2.

* * * * *

UNITED STATES PATENT AND TRADEMARK OFFICE
CERTIFICATE OF CORRECTION

PATENT NO. : 4,639,467
DATED : January 27, 1987
INVENTOR(S) : Celino, deceased, et al.

It is certified that error appears in the above—identified patent and that said Letters Patent is hereby corrected as shown below:

At [54], in the title, delete the word "CRISMAICIN" and insert the word --CRISAMICIN-- therefor.

In column 1, in the formula, at line 48, insert -- -- -- beside each instance of the letter H as in the formula in columns 5 and 6.

In column 3, at line 54, insert --10-- after "X" and before "-3".

Signed and Sealed this

Twenty-eighth Day of April, 1987

Attest:

DONALD J. QUIGG

Attesting Officer

Commissioner of Patents and Trademarks